United States Patent [19]

Watanabe

[11] Patent Number: 5,032,110
[45] Date of Patent: Jul. 16, 1991

[54] ELECTROTHERAPEUTICAL DEVICE

[75] Inventor: Tsutomu Watanabe, Usuki, Japan

[73] Assignees: Wataru Watanabe; Yozo Niina, Usuki, Japan

[21] Appl. No.: 446,290

[22] Filed: Dec. 5, 1989

[51] Int. Cl.$^5$ .............................................. A61N 1/30
[52] U.S. Cl. ...................................... 604/20; 128/803
[58] Field of Search .......................... 604/20; 128/803

[56] References Cited

U.S. PATENT DOCUMENTS

| | | | |
|---|---|---|---|
| 4,474,570 | 10/1984 | Ariura et al. | 604/20 |
| 4,713,050 | 12/1987 | Sibalis | 604/20 |
| 4,725,263 | 2/1988 | McNichols et al. | 604/20 |
| 4,911,688 | 3/1990 | Jones | 604/20 |

FOREIGN PATENT DOCUMENTS

| | | | |
|---|---|---|---|
| 0225556 | 6/1987 | European Pat. Off. | 604/20 |
| 0318776 | 6/1989 | European Pat. Off. | 128/803 |

Primary Examiner—Lee S. Cohen
Attorney, Agent, or Firm—Wenderoth, Lind & Ponack

[57] ABSTRACT

An electrotherapeutic device includes a small-sized flat primary cell provided on top and bottom thereof with electrodes insulated from each other by an electrical insulating layer. A covering sheet is provided to enclose the first and second electrodes and the primary cell to define a gap therebetween. A medicine having conductivity and fluidity is introduced into the gap through its bottom opening. A peelable sheet is stuck on the peripheral portion of the covering sheet to seal a medicine in the gap.

3 Claims, 1 Drawing Sheet

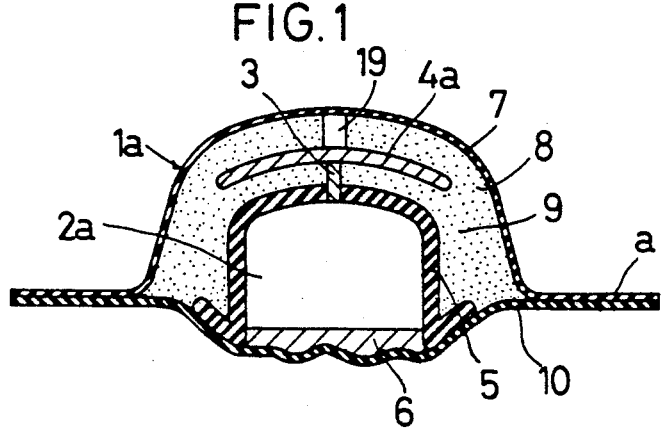
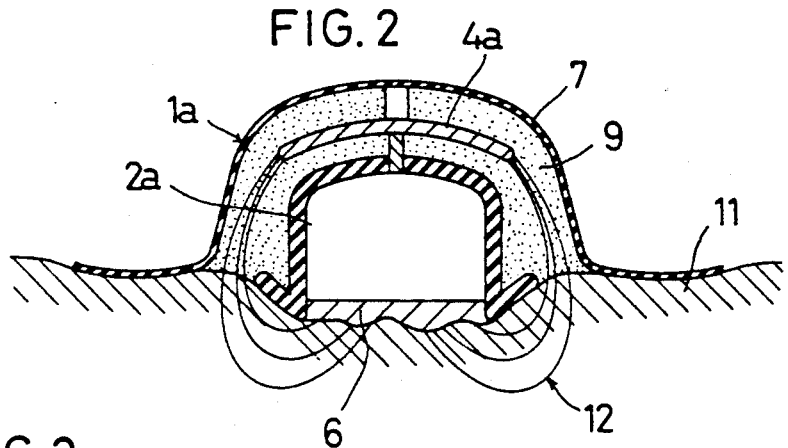
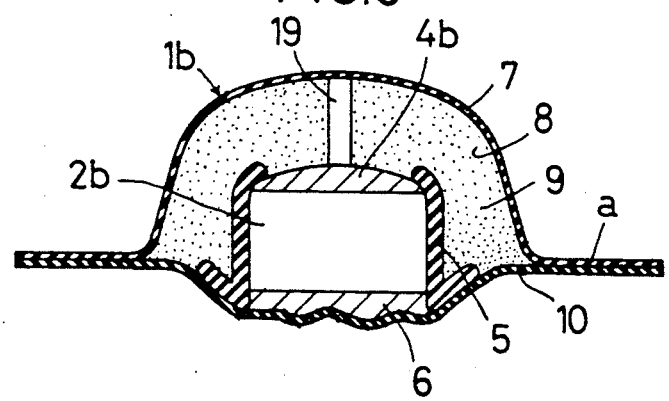
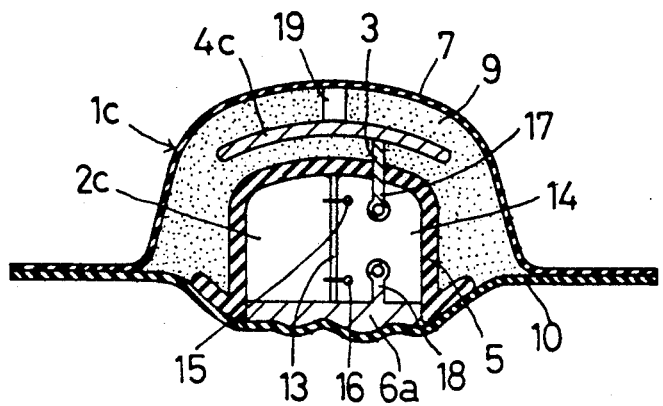

ELECTROTHERAPEUTICAL DEVICE

BACKGROUND OF THE INVENTION

The present invention relates to an electrotherapeutical device, especially an iontophoretic electrotherapeutical device.

There is known an iontophoretic electrotherapeutical device for use in the treatment of neuralgia, stiff shoulders, headaches, muscleaches and sprains (Japanese Utility Model Publication 55-14343).

This device comprises a body provided with an anode terminal and a cathode terminal, lead wires connected to the anode and cathode terminals, and terminal members connected to the leading ends of the lead wires. Each terminal member is provided with an electrode to which a holder is fixed. In the holder are received blocks impregnated with a conductive liquid. The block to be directly applied to the affected part is impregnated with a therapeutic medicine.

The device is switched on with one of the terminal members put right on the affected area and the other on the opposite side thereof. The liquid medicine is ionized and absorbed into the patient's body through tissue under the skin.

This type of prior art electrotherapeutical device has a rather large size, because it requires the anode and cathode terminal members in addition to the power source and the body. Also, this device required an operator other than a patient. Furthermore the patient is deprived of freedom of movement during electrotherapy.

SUMMARY OF THE INVENTION

It is an object of the present invention to provide an electrotherapeutic device which is compact and obviates the abovesaid shortcomings.

In accordance with the present invention, there is provided an electrotherapeutic device comprising a flat primary cell; first and second electrodes; an electrical insulating means for insulating the first and second electrodes from each other; a covering sheet provided to enclose the first and second electrodes and the primary cell so as to define a gap therebetween, the gap being filled with a therapeutic medicine having conductivity and fluidity; and a peelable sheet stuck on the covering sheet at the peripheral portion thereof to seal the therapeutic medicine in the gap.

According to another aspect of the present invention, there is provided an electrotherapeutic device comprising a primary cell; a low-frequency generator provided in juxtaposition with the primary cell and having its input terminals connected to the primary cell; first and second electrodes connected to output terminals of the low-frequency generator; an electrical insulating means for insulating the first and second electrodes from each other; a covering sheet provided to enclose the first and second electrodes and the primary cell and the low-frequency generator to define a gap therebetween; the gap being filled with a therapeutic medicine having conductivity and fluidity; and a peelable sheet stuck on the covering sheet at the peripheral portion thereof to seal the therapeutic medicine in the gap.

The electrotherapeutic device according to the present invention is compact because its body (power supply) is in the form of a flat and small primary cell and the parts corresponding to the terminal members of a prior art device are built-in electrodes. Simply by pressing the exposed surface of one of the electrodes on the skin of a patient after peeling away the sheet closing the gap filled with medicine, the current generated by the cell will flow between the electrodes through the patient's tissue under the skin, thus allowing the ionized medicine to be easily absorbed into the body through the skin.

Further, the device according to the present invention can be easily and stably attached to the skin of a patient by means of a sticking plaster or by sticking the peripheral portion of the covering sheet on the skin. This will make it possible not only for the patient to move freely during the iontophoretic therapy, but also to maintain its medical effect even while the patient is asleep.

Other features and objects of the present invention will become apparent from the following description taken with reference to the accompanying drawings, in which:

BRIEF DESCRIPTION OF THE PREFERRED EMBODIMENT

FIG. 1 is a vertical sectional view of the first embodiment of the present invention;

FIG. 2 is a similar view showing the device in use;

FIG. 3 is a vertical sectional view of the second embodiment; and

FIG. 4 is a similar view of the third embodiment.

DETAILED DESCRIPTION OF THE PREFERRED EMBODIMENT

FIG. 1 shows the first embodiment of the present invention in which an electrotherapeutic device 1a comprises a flat and small primary cell 2a such as a button-shaped mercury cell having its top surface covered with an electrical insulating layer 5, a plate-shaped electrode 4a (e.g. anode) provided over the cell 2a and connected to the cell through a terminal 3 extending through the insulating layer 5, and another electrode 6 (e.g. cathode) provided on the bottom of the cell 2a so as to extend in parallel with the electrode 4a. The electrode 6 and the electrode 4a are insulated from each other by the peripheral portion of the insulating layer 5.

A covering sheet 7 is put over the electrode 4a at the side opposite to the electrical insulating layer 5 and is preferably spaced therefrom by a pillar 19 and has its outer peripheral portion extending in parallel with the peripheral portion of the electrical insulating layer 5 to define a square 8 therebetween. After filling a space 8 formed between the electrical insulating layer 5 and the covering sheet 7 with a fluidic, conductive therapeutic medicine 9, the opening of the space 8 is closed by a sheet 10 of non-conductive material which is removably adhesively attached to electrode 6 and covering sheet 7 so that it can easily be peeled off.

The covering sheet 7 is provided along its edge with an outwardly extending flange a. The sheet 10 has an area large enough to cover the electrode 6 and overlap the flange a of the sheet 7 and has its peripheral surface opposite to the flange a treated with a weak release material. The flange a of the sheet 7 is bonded to the flange of the sheet 10 through a pressure-sensitive adhesive layer (not shown) formed on the flange a to seal the medicine 9 in the space 8.

The medicine 9 should be powdery or liquid so as to be easily introduced into the space 8. If the medicine is not conductive, it is necessary to add a conductive liquid.

In operation, as shown in FIG. 2, the electrotherapeutic device 1a is stuck right on the affected part of the skin 11 of the patient.

Before sticking the electrotherapeutic device 1a on the skin 11, the sheet 10 is peeled off and a conductive liquid (not shown) is applied to the exposed side of the electrode 6.

The electrotherapeutic device 1a is stuck on the skin 1 through the pressure-sensitive adhesive layer provided on the flange a of the covering sheet 7 (if such an adhesive layer is provided). Alternatively or in addition thereto, an adhesive tape or the like (not shown) having a larger area than the electrotherapeutic device 1a should be put thereon to stably hold it in position.

In this state, the current generated by the primary cell 2a flows between the electrodes 4a and 6 through the medicine 9 in the space 8 and the affected area under the skin as indicated by numeral 12. Thus the medicine 9 will be ionized and permeate the skin so as to be absorbed under the skin.

FIG. 3 shows the second embodiment in which an electrode 4b is connected directly to the primary cell 2b. The covering sheet 7 is supported by a pillar 19. Otherwise, the electrotherapeutic device 1b in this embodiment is the same in structure as that in the first embodiment.

FIG. 4 shows the third embodiment in which an electrotherapeutic device 1c includes a small primary cell 2c and a small low-frequency generator 14 juxtaposed to each other through an electrical insulating layer 13. The low-frequency generator 14 has its input poles 15 and 16 connected to the cell 2c and has its output poles 17 and 18 connected to an electrode 4c provided over the cell 2c and the low-frequency generator 14 and another electrode 6a provided on the bottom thereof, respectively. Otherwise, this embodiment is the same in structure as the first embodiment.

In this embodiment, by the provision of the low-frequency generator, low-frequency pulses will be applied to the affected area to stimulate it. This will activate the bloodstream and quicken the absorption of medicine.

What is claimed is:

1. An electrotherapeutic device comprising:
   a current source having first and second electrodes spaced from each other;
   an electrical insulating means extending around the outside of said current source for insulating said first and second electrodes from each other;
   a covering sheet around said current source and said insulating means and defining a single chamber having one side open and within which said current source and insulating means are positioned spaced from said covering sheet to define a gap therebetween opening out of said open side of said chamber adjacent said current source and with said first electrode facing out of said one side of said chamber and said second electrode being within said chamber;
   a therapeutic medicine having conductivity and fluidity filling said gap and contacting said second electrode; and
   a protective sheet removably adhered at least to a peripheral portion of said covering sheet around said one side and covering said one side to seal said therapeutic medicine in said gap.

2. An electrotherapeutic device as claimed in claim 1 in which said current source is a primary cell.

3. An electrotherapeutic device as claimed in claim 1 in which said current source is a primary cell and a low frequency generator provided in juxtaposition to said primary cell and having input terminals connected to said primary cell, said first and second electrodes being connected to output terminals of said low-frequency generator.

* * * * *